United States Patent [19]

Hearn

[11] Patent Number: 4,510,336

[45] Date of Patent: Apr. 9, 1985

[54] TRANSETHERIFICATION METHOD

[75] Inventor: Dennis Hearn, Houston, Tex.

[73] Assignee: Chemical Research & Licensing Company, Houston, Tex.

[21] Appl. No.: 435,459

[22] Filed: Oct. 20, 1982

[51] Int. Cl.³ .................................... C07C 41/14
[52] U.S. Cl. ............................ 568/697; 568/866
[58] Field of Search ........................ 568/697, 700

[56] References Cited

U.S. PATENT DOCUMENTS

| | | | |
|---|---|---|---|
| 3,629,478 | 12/1971 | Haunachild | 568/497 |
| 4,198,530 | 4/1980 | Smith | 568/497 |
| 4,215,011 | 7/1980 | Smith | 568/497 |
| 4,232,177 | 11/1980 | Smith | 568/497 |
| 4,242,530 | 12/1980 | Smith | 568/497 |
| 4,250,052 | 2/1981 | Smith | 568/497 |
| 4,302,298 | 11/1981 | Mikitenko et al. | 568/497 |
| 4,302,356 | 11/1981 | Smith | 568/497 |
| 4,307,254 | 12/1981 | Smith | 568/497 |
| 4,324,924 | 4/1982 | Torck et al. | 568/497 |
| 4,334,890 | 6/1982 | Kochar et al. | 568/497 |
| 4,336,407 | 6/1982 | Smith | 568/497 |

Primary Examiner—Werren B. Lone
Attorney, Agent, or Firm—Kenneth H. Johnson

[57] ABSTRACT

Transetherification is carried out in a catalytic distillation reactor, wherein the catalytic structure also serves as a distillation structure, by feeding a first ether to the catalyst bed to at least partially dissociate it into a first olefin and a first alcohol while concurrently therewith feeding either a second olefin (preferably a tertiary olefin) having a higher boiling point than said first olefin or a second alcohol having a higher boiling point than said first alcohol to the catalyst whereby either the second olefin and the first alcohol or the first olefin and the second alcohol react to form a second ether which has a higher boiling point than the first ether, which second ether is concurrently removed as a bottoms in the concurrent reaction-distillation to force that reaction to completion, while the unreacted first olefin or first alcohol is removed in the overhead.

14 Claims, 1 Drawing Figure

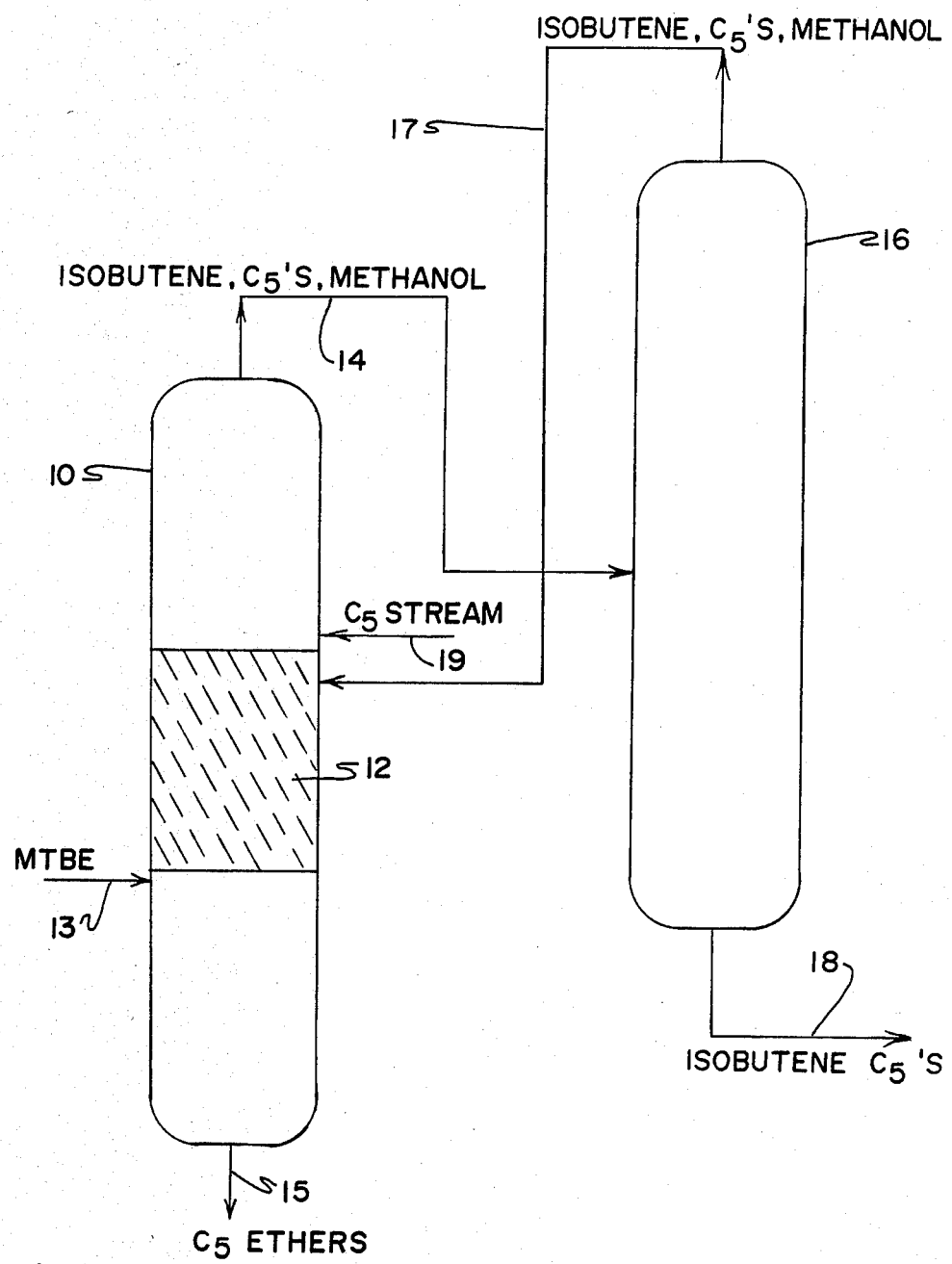

TRANSETHERIFICATION METHOD

The Government of the United States of America has certain rights in this invention pursuant to Contract No. DE-FC07-80CS40454 awarded by the US Department of Energy.

BACKGROUND OF THE INVENTION

The present invention relates to a method of transetherification in a concurrent reaction distillation column reactor.

RELATED ART

The process of concurrent reaction and distillation of the reaction components using the reaction catalyst as the distillation structure is known as catalytic distillation and is described along with suitable catalyst structures in several commonly assigned U.S. patents, including U.S. Pat. Nos. 4,215,011; 4,232,177; 4,242,530; 4,250,052; 4,302,356; 4,307,254 and 4,336,407

Among the attributes of this process are:

(1) The utilization of a single reactor for carrying out the reaction and the initial distillation of the reaction mixture. Thus, initial investment in new equipment is substantially lower than liquid phase reactors and separate distillation towers. However, this aspect of the catalytic distillation gives rise to a further capital investment advantage in that the system can be retrofitted into existing distillation towers at a substantial savings in cost and time. This is an important consideration, since most refineries have unused or expendable distillation towers adequately suited for retrofitting.

(2) The catalytic reaction is very likely exothermic, such as the etherifications and in those reactions where it is, the heat of the reaction is used for the distillation (and supplemented by added heat as necessary).

(3) In exothermic reactions, such as etherifications and transetherifications, the heat of the reaction has been a problem, since in conventional reactions the heat must be dispersed or the reaction becomes a runaway, produces undesired by-products and certain types of catalyst can be damaged.

In the catalytic distillation, excess heat merely causes more boil-up and hence by controlling the pressure, the temperature in the reactor is controlled and the heat of reaction is utilized as desired. Thus, in commercial scale the present process has proven very easy to start up, control and shut down. In other words, the reaction system has the ease and simplicity of operation of a distillation.

(4) The simultaneous reaction and distillation occurring within the catalyst structure results in disruption of a reaction equilibrium and forces the reaction to completion.

The preparation of ethers from $C_4$ and $C_5$ refinery streams is obtainable by various methods such as disclosed in U.S. Pat. Nos. 3,629,478; 4,198,530; 4,039,590; 4,307,254 and 4,336,407.

It has also been proposed that high purity isobutene can be prepared by dissociation of methyl tertiary butyl ether, however, in that process, the products are isobutene and methanol. The methanol must be recovered and used in some manner. It is an advantage of the present invention that useful higher ethers are formed, utilizing the methanol. It is a further advantage that the isoolefins can be removed from streams containing corresponding chain length normal olefins, which separations are usually difficult to obtain by distillation.

It is a further feature of the present invention shared with other reactions carried out by catalytic distillation that a somewhat lower amount of energy is required since the heat of reaction is used to provide boil up in the distillation.

These and other advantages will become apparent from the following descriptions and discussion.

SUMMARY OF THE INVENTION

Briefly, the present invention is a method for transetherification wherein an organic ether is fed to acidic cation exchange resin in a reactor where the catalyst also serves as the distillation structure, where the ether is partially dissociated into its olefin and alcohol components. Concurrently either a higher boiling olefin or a higher boiling alcohol is fed into the catalyst bed. A second ether having a higher boiling point than the first ether (and usually the other materials in the reaction mixed) is formed, e.g., the higher boiling alcohol forms an ether with the dissociated olefin component or the higher boiling olefin forms an ether with the dissociated alcohol component. Since the second ether is the highest boiling component of the reaction mixture, it will drop to the bottom of the reactor since a distillation is going on concurrently in the catalyst bed, thus the reaction, transetherification, is forced to completion by removal of heavier ether (second) product as bottoms.

The other components, e.g., diluents or feed stream components of either the higher boiling olefins or the higher boiling alcohol and the unreacted portion of the dissociated first ether are usually lighter than the second ether and removed from the reactor as overhead. However, in some operations it may be that some of the unreacted materials are removed as part of the bottoms with the second ether.

The higher boiling olefin or higher boiling alcohol are preferably present in a stoichiometric amount, based on the first ether in order to react with all of the dissociate component (either olefin or alcohol), otherwise, some of these materials may be lost in the overhead.

The present invention is an excellent means of producing more difficultly produced ethers from easily produced ethers. For example, the symmetrical ethers, such as diethyl ether, are easily produced but unsymmetrical ethers such as ethyl hexyl ether are difficult to produce. Using diethyl ether as one feed and hexanol as the other feed, ethyl hexyl ether can be produced in very high yields and in very high purity.

Thus in one embodiment there is a method of transetherification comprising concurrently:

(a) feeding a first ether to a distillation column reactor, (b) contacting said first ether with a fixed bed acidic cation exchange resin which is a distillation structure to thereby at least partially dissociate said first ether into an alcohol and a first olefin, (c) feeding a second olefin having a higher boiling point than said first olefin to said fixed bed, preferably a stoichiometric amount based on said first ether, (d) reacting said second olefin with said alcohol to form a second ether having a higher boiling point than said first ether, (e) fractionating the resultant second ether from unreacted materials, (f) withdrawing said second ether from the distillation column reactor as a bottoms, and (g) withdrawing unreacted materials as an overhead. In this embodiment the unreacted materials will include the first olefin, any unreacted alcohol, unreacted second olefin and any other components lighter than the second ether which may have been present in the feed streams.

In a particular aspect of this embodiment, the second olefin is a tertiary olefin. Tertiary olefins are highly reactive and would be especially desirable if the first ether were the reaction product of a tertiary olefin and an alcohol, such as methyl tertiary butyl ether (MTBE). In that case the transetherification would proceed best with a $C_5+$ tertiary olefin as the second olefin.

In another embodiment there is a method of transetherification comprising concurrently:

(a) feeding a first ether to a distillation column reactor, (b) contacting said first ether with a fixed bed acidic cation exchange resin which is a distillation structure to thereby at least partially dissociate said first ether into a first alcohol and an olefin, (c) feeding a second alcohol having a higher boiling point than said first alcohol to said fixed bed, preferably a stoichiometric amount based on said first ether, (d) reacting said second alcohol with said olefin to form a second ether having a higher boiling point than said first ether, (e) fractionating the resultant second ether from unreacted materials, (f) withdrawing said second ether from the distillation column reactor as a bottoms, and (g) withdrawing unreacted materials overhead. In this embodiment the unreacted materials will include the first alcohol, any unreacted olefin, unreacted second alcohol and any other components lighter than the second ether which may have been present in the feed streams.

In order to insure the best contact of materials for the present reaction, the lowest boiling feed material is fed at the lower end of the catalytic distillation bed and the highest boiling feed material at the upper end. The temperature in the bed is maintained at the boiling point of the lowest boiling material of the composition at a given pressure in the tower. This is a result of the concurrent distillation and is a natural law.

In some instances the highest boiling feed material will be the first ether with the second olefin or second alcohol being lower boiling, e.g., if the first ether is MTBE and the second alcohol is propanol, the first ether is highest boiling, however, if the second alcohol is 1-hexanol, the hexanol is the higher boiling material.

The second olefin or the second alcohol may be any of those which are liquids and which are vaporized within the safe temperature range for the catalyst, e.g., up to about 180 degrees C. for the Amberlyst 15, and possibly to somewhat over 200 degrees C. for some of the newer resin catalysts.

In one specific embodiment the first ether is MTBE and a tertiary $C_5$–$C_{10}$ olefin is the second olefin. The second olefin may be a component of hydrocarbon stream or cut, which will normally comprise predominantly a single chain length in the $C_5$ to $C_{10}$ range. This is a practical matter since hydrocarbons of the same length generally boil over a relatively close range, and a cut is usually taken to encompass that range of hydrocarbons. However, a particular cut, e.g., $C_5$ may contain up to 10 mole % of the adjacent chain length hydrocarbons, e.g., $C_4$'s and $C_6$'s. Also, the narrower cuts restrict the tertiary olefin present to those of the chain cut, hence when these compound preferentially form ethers, the ethers will have a higher boiling point than the unreacted hydrocarbon feed and the isobutene, allowing an easy distillation between the ether and the hydrocarbons, whereas in a highly mixed stream some of the higher hydrocarbons may have higher boiling points than the lower ethers, hence an ether-hydrocarbon separation would not be effected.

The overhead from this transetherification is isobutene admixed with the unreacted $C_5$ to $C_{10}$ hydrocarbons. The separation of isobutene from the other hydrocarbons presents no problem by straight distillation.

The amount of MTBE present in the reactor should be sufficient to transetherify the tertiary olefin if it is the desired result to remove them from the hydrocarbon stream, which amount would be stoichiometric or excess thereof. In some situations it may be desirable to add methanol to force the transetherification.

It is also likely that some methanol will be freed and not reacted with any unsaturated olefin, just as in the initial etherification of the isobutene. Hence some methanol may be carried overhead with the hydrocarbons, which may be removed by conventional water washing. The amount of methanol carried overhead can be reduced by conducting the distillation at two pressures. That is, the reaction distillation is conducted at a higher pressure (100–200 psig) to favor the reaction and a second stage of the distillation, wherein the overhead from the first stage is fractionated, is conducted at lower pressure (0 to 100 psig) to reduce methanol in the overhead azeotrope. This procedure is defined in detail in commonly assigned U.S. patent application Ser. No. 349,043 filed Feb. 16, 1982, which is incorporated herein.

BRIEF DESCRIPTION OF THE DRAWING

The FIGURE is a schematic representation of a transetherification process.

DETAILED DESCRIPTION OF THE INVENTION

In the case of the transetherification using a second olefin these will generally have 3 to 10 carbon atoms, such as propene, isobutene, n-butene, 2-methylbutene-1, 2-methylpentene-1, 2-ethylpentene-1, 2,4,4-trimethylpentene-1, 2-methyloctene-1, and the like. The tertiary olefins are preferred because of their greater activity.

The amount of the reactive second tertiary olefin present in the $C_5$ to $C_{10}$ stream can vary widely, but usually would be about 5 to 60 mole % of the stream. Since the MTBE stream would be a high purity stream the feed rate on the $C_5$ to $C_{10}$ would be adjusted to provide a substantially stoichiometric amount of the reactive $C_5$ to $C_{10}$ olefins for the transetherification. However, the second olefin need not be diluted and may be fed to the reactor as a substantially pure stream.

The tertiary olefins are preferentially etherified, leaving the particular stream with such compounds reduced (and preferably eliminated). The ethers have higher boiling points than the remaining hydrocarbon stream and the isobutene. Thus, the residual hydrocarbons from the stream and isobutene can be removed overhead and the ethers as a bottom fraction.

The $C_5$ ethers are gasoline octene improvers and all of these ethers are excellent solvents.

In the case of the transetherification using a second alcohol, these will generally have 2 to 11 carbon atoms, such as ethanol, propanol, n-butanol, 1-hexanol, 1-hendecanol and the like.

The reaction system can be described as heterogeneous, since the catalyst remains a distinct entity. The catalyst may be employed in such conventional distillation packing shapes, as Raschig rings, Pall rings, saddles or the like. Similarly, the resin may be employed in a granular or bead form as described herein.

It has been found that the resin beads in a conventional fixed bed form too compact a mass for the upward flowing vapor and downward flowing liquid. However, it has been found that placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attrition. This novel catalyst arrangement is described in detail in commonly owned U.S. Pat. No. 4,242,530 which is incorporated herein.

The cloth may be of any material which is not attacked by hydrocarbon feed, the catalyst or products under the conditions of the reaction. Cotton or linen may be useful, but fiber glass cloth or "Teflon" cloth are preferred. Briefly, a preferred catalyst system comprises a plurality of closed cloth pockets arranged and supported in said distillation column reactor by wire mesh intimately associated therewith.

The particular catalytic material may be powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials and of course affects the activity of the catalytic material).

The transetherification reaction with higher olefins or higher alcohols and the fractionation of the resultant hydrocarbon ether mixture is carried out simultaneously, i.e., concurrently. That is, as the second ether is formed in the catalyst bed, the lower boiling hydrocarbons are fractionated away in the catalyst bed and removed overhead while the high boiling (second) ether drops to the lower portion of the column.

The bulk type liquid phase reactions of the prior art had as one problem the control of the temperature. The distillation avoids this problem entirely.

The success of the catalytic distillation approach lies in an understanding of the principles associated with distillation. First, because the reaction is occurring concurrently with distillation, the initial reaction is occurring concurrently with distillation, the initial reaction product, e.g., trans ether is removed from the reaction zone nearly as quickly as it is formed. This removal of the ether minimizes decomposition of the ether and chaining to form polymer. Second, because all the hydrocarbon components are boiling, the temperature of the reaction is controlled by the boiling point of the hydrocarbon mixture at the system pressure. The heat of the reaction simply creates more boil up, but no increase in temperature. Third, the reaction has an increased driving force because the reaction products have been removed and cannot contribute to a reverse reaction (LeChatelier's Principle).

As a result, a great deal of control over the rate of reaction and distribution of products can be achieved by regulating the system pressure. Also, adjusting the through-put (residence time = liquid hourly space velocity$^{-1}$) gives further control of product distribution.

The temperature in the reactor is determined by the boiling point of the reaction materials at any given pressure. This, of course, refers to the overhead temperature in the column, and the temperature in the lower portions of the column will reflect the constitution of the material in that part of the column. At constant pressure a change in the temperature of the system, indicates a change in the composition in the column. Thus, to change the temperature, the pressure is changed. By increasing the pressure, the temperature in the system is increased. Generally, pressures in the range of 0 to 400 psig are or may be employed.

The reaction of olefins, with alcohol, e.g., methanol, is equilibrium limited; however, by carrying out the reaction in a distillation column reactor and fractionating the formed product, e.g., the second ether drops downward away from the reaction zone, the equilibrium is constantly disrupted and hence the reaction never comes to equilibrium. This has the advantage, of course, of achieving and effective 100% conversion, provided the catalyst bed is of sufficient length such that none of the higher olefins escape therefrom to go overhead with the unreacted material. The adjustment of the size of the catalyst bed is a mere mechanical step to be determined for each reactor and in accordance with the reaction conditions.

The ether system would normally be considered anhydrous; however, small amounts of water often saturate the feed stream and represent about 400 to 600 ppm thereof. The process will continue to operate in the same fashion, in the presence of this amount of water. Generally, the system will be employed with less than 1 mole % water in the feed.

A reflux is preferably included in the system. The reflux ratio could vary over the rate of 0.5 to 20:1. In practice, the higher ratio may be used to compensate for a short catalyst bed such as required for experimental work. In commercial size units the catalyst bed would be provided so that lower reflux and hence higher unit productivity could be obtained.

Catalysts suitable for the present transetherification process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0 to 150 degrees C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat Nos. 3,784,399; 3,770,567 and 3,849,243.

In addition to pockets of resin catalyst described, cation exchange resin structures prepared by the process described in copending, commonly owed U.S. Pat. No. 4,250,052 which is incorporated herein, may be employed.

The invention can be understood from a consideration of the drawing. In this embodiment the ether feed is MTBE and the higher chain length feed is a $C_5$ stream containing 2-methyl butene-1 and 2-methyl butene-2 (isoamylene isomers) which is fed to the distillation reactor 10 via 19 at a point immediately above the catalyst bed 12. The $C_5$ stream enters the catalyst bed where it contacts the catalyst and the MTBE entering the catalyst bed via 13 (at the lower end).

The catalyst bed is described in U.S. Pat. Nos. 4,215,015 and 4,302,356 and consist of fiber glass belts having vertical pockets therein containing Amberlyst 15 (Rohm and Haas) acidic cation exchange resin beads therein, with each belt formed into a spiral by wrapping it around stainless steel demister wire. Thus, the catalyst bed is also a distillation structure.

The MTBE contacts the catalyst and dissociates into isobutene and methanol. This dissociation is also equilibrium limited, however, the methanol thus liberated also contacts the isoamylene and forms the corresponding ethers (an equilibrium limited reaction). The reactions are exothermic and some additional heat is supplied via conventional means such as a reboiler (not shown) to have a vaporous phase which contains the isobutene and normal $C_5$ mono olefins, and $C_5$ alkanes, which forces the MTBE dissociation. Concurrently, the higher boiling $C_5$ ethers drop out of the catalyst bed, thereby inhibiting the dissociation of the $C_5$ and forcing that etherification to completion. The reactor distillation column is operated at 70 psig in this embodiment.

The $C_5$ ethers are removed via line 1. These ethers are substantially free of methanol. The overhead 14 contains the isobutene, unreacted $C_5$'s (normal monoolefins and alkanes) and some azeotroped methanol. This is fed to distillation tower 16 which is operated at 200 psig thereby resulting in an azeotrope overhead 17 containing substantially all of the methanol and some of the isobutene and $C_5$ which is recycled via 17 into the catalyst bed 12.

The bottoms from tower 16 are a mixed isobutene-$C_5$ stream which may be easily distilled to produce a high purity isobutene and a $C_5$ stream substantially free of isoamylene.

The invention claimed is:

1. A method of transetherification comprising concurrently:
    (a) feeding a first ether capable of dissociating into a first olefin and an alcohol and having a boiling point at pressure in the range of 0 to 400 psig to a distillation column reactor,
    (b) contacting said first ether with a fixed bed acidic cation exchange resin which is a distillation structure to thereby at least partially dissociate said first ether into an alcohol and first olefin,
    (c) feeding a second olefin having 3 to 10 carbon atoms and a higher boiling point than said first olefin to said fixed bed, whereby said second olefin reacts with said alcohol to form a second ether having a higher boiling point than said first ether,
    (d) fractionating the resultant second ether from unreacted materials,
    (e) withdrawing said second ether from the distillation column reactor as a bottoms,
    (f) withdrawing unreacted materials as an overhead.

2. The method according to claim 1 wherein said second olefin is a tertiary olefin.

3. The method according to claim 1 wherein a stoichiometric amount of said second olefin based on said first ether is fed.

4. The method according to claim 2 wherein a stoichiometric amount of said second olefin based on said first ether is fed.

5. The method according to claim 1 wherein the highest boiling feed to the distillation column reactor is fed at the upper end of the fixed bed and the lowest boiling feed to the distillation column reactor is fed at the lower end of the fixed bed.

6. The method according to claim 4 wherein methyl tertiary butyl ether is the first ether, isobutene is the first olefin, methanol is the alcohol, isoamylene is the second olefin and isoamyl ether is the second ether.

7. The method according to claim 6 wherein methyl tertiary butyl ether is fed at the lower end of the fixed bed and isoamylene is fed at the upper end of the fixed bed.

8. The method according to claim 7 wherein said isoamylene is a component of a $C_5$ hydrocarbon stream.

9. The method according to claim 1 wherein said first olefin is withdrawn in said overhead.

10. The method of transetherification comprising concurrently:
    (a) feed a first ether capable of dissociating into an olefin and a first alcohol and having a boiling point at a pressure in the range of 0 to 400 psig to a distillation column reactor, (b) contacting said first ether with a fixed bed acidic cation exchange resin which is a distillation structure to thereby at least partially dissociate said first either into a first alcohol and an olefin, (c) feeding a second alcohol having 2 to 11 carbon atoms and a higher boiling point than said first alcohol to said fixed bed, whereby said second alcohol reacts with said olefin to form a second ether having a higher boiling point than said first ether, (d) fractionating the resultant second ether from unreacted materials, (e) withdrawing said second ether from the distillation column (f) withdrawing unreacted materials as an overhead.

11. The method according to claim 10 wherein a stoichiometric amount of said second alcohol based on said first ether is fed.

12. The method according to claim 11 wherein a stoichiometric amount of said second alcohol based on said first ether is fed.

13. The method according to claim 10 wherein the highest boiling feed to the distillate column reactor is fed at the upper end of the fixed bed and the lowest boiling feed to the distillation column reactor is fed at the lower end of the fixed bed.

14. The method according to claim 10 wherein said first alcohol is withdrawn in said overhead.

* * * * *